United States Patent [19]
Tamano et al.

[11] Patent Number: 5,811,834
[45] Date of Patent: Sep. 22, 1998

[54] LIGHT-EMITTING MATERIAL FOR ORGANO-ELECTROLUMINESCENCE DEVICE AND ORGANO-ELECTROLUMINESCENCE DEVICE FOR WHICH THE LIGHT-EMITTING MATERIAL IS ADAPTED

[75] Inventors: Michiko Tamano; Toshio Enokida, both of Tokyo, Japan

[73] Assignee: Toyo Ink Manufacturing Co., Ltd., Toyko, Japan

[21] Appl. No.: 788,436

[22] Filed: Jan. 28, 1997

[30] Foreign Application Priority Data

Jan. 29, 1996 [JP] Japan ..................................... 8-012488

[51] Int. Cl.[6] ............................. H01L 35/24; H01L 51/00
[52] U.S. Cl. ............................. 257/40; 357/103; 313/504
[58] Field of Search ....................... 257/40, 103; 313/504

[56] References Cited

U.S. PATENT DOCUMENTS 4,672,265 6/1987 Eguchi et al. ........................... 313/504
5,281,489 1/1994 Mori et al. .............................. 428/690

FOREIGN PATENT DOCUMENTS 650 955  5/1995  European Pat. Off. .
681 019  11/1995 European Pat. Off. .
757 088  2/1997  European Pat. Off. .

OTHER PUBLICATIONS

Toyo Ink, Database WPI Section Ch week 9618, Derwent Publications, London, England XP002030009 JP 08 053 387 27 Feb. 1996.

Sapochak et al., Polymeric Materials Science and Engineering, vol. 72 (1995), pp. 331–332 XP000671148 No date.

*Primary Examiner*—Sara W. Crane
*Attorney, Agent, or Firm*—Wenderoth, Lind & Ponack

[57] ABSTRACT

A light-emitting material for developing an organic EL device, which has the formula [1] or [2] recited in claims, and an organic EL device having layers thereof, the organic EL device having a high light emission brightness and a long life of light emission.

9 Claims, 3 Drawing Sheets

LIGHT-EMITTING MATERIAL FOR ORGANO-ELECTROLUMINESCENCE DEVICE AND ORGANO-ELECTROLUMINESCENCE DEVICE FOR WHICH THE LIGHT-EMITTING MATERIAL IS ADAPTED

FIELD OF THE INVENTION

The present invention relates to a light-emitting material for an organo-electroluminescence ("EL" hereinafter) device used as a flat light source or display, and to a light-emitting device having a high brightness.

PRIOR ART OF THE INVENTION

An EL device using an organic substance is greatly expected to be usable as a solid light-emitting inexpensive large-screen, full-color display device, and the development thereof is being made in many ways. Generally, an EL device is composed of a light-emitting layer and a pair of mutually opposite electrodes sandwiching the light-emitting layer. The light emission by an EL device is the following phenomenon. When an electric field is applied between these two electrodes, the cathode injects electrons into the light-emitting layer, and the anode injects holes into the light-emitting layer. When the electrons recombine with the holes in the light-emitting layer, their energy level shifts to a valence bond band to release energy as fluorescent light.

As compared with inorganic EL devices, conventional organic EL devices require high voltage, and their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect of emitting light at a low voltage as low as less than 10 V, and it attracts attention (Appl. Phy. Lett., Vol. 51, page 913, 1987). The above organic EL device has a fluorescent layer containing a metal chelate complex and a hole-injecting layer containing an amine-based compound, and emits green light having a high brightness. The above organic EL device achieves nearly practically usable performance, since it accomplishes a brightness of 1,000 cd/m$^2$ and a maximum light emission efficiency of 1.5 lm/W at a direct current voltage of 6 or 7V.

However, conventional organic EL devices including the above organic EL device are not yet satisfactory in brightness although these organic EL devices are improved in brightness to some extent. Further, the serious problem is that they are insufficient in light emission stability in their continuous operation for a long period of time. That is because, for example, a metal chelate complex such as a tris(8-hydroxyquinolinate)aluminum complex (Alq3) is chemically unstable at a time of field light emission, is poor in adhesion to a cathode and extremely deteriorates in a short period of emission.

As a blue light emitting material for an organic EL device, further, there have been proposed materials having a structure of anthracene, tetraphenylbutadiene, stilbene, bisstyryl, cyclopentadiene or oxadiazole, while these materials are insufficient in light emission efficiency and maximum light emission brightness and have problems when practically used ("Yuuki EL Sosi Kaihatsu Senryaku (Strategy for Development of organic El Devices)", issued by K.K. Science Forum, page 169, 1992).

For the foregoing reasons, it is desired to develop a light-emitting material having an excellent light emission capacity and durability for developing an organic EL device which has a high light emission brightness and can perform a light emission for a long period of time.

SUMMARY OF THE INVENTION

It is an object of the present invention to provide an organic EL device having a high light emission brightness and a long life of light emission.

According to the present invention, there is provided a light-emitting material for developing an organic EL device, which has the formula [1],

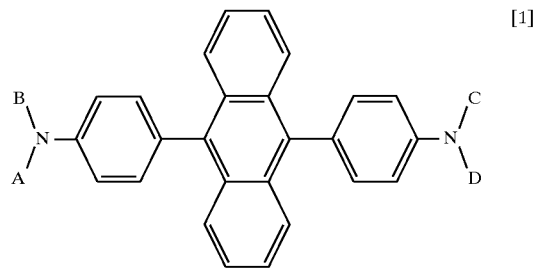

[1]

wherein each of A to D is a substituted or nonsubstituted alkyl group, a substituted or nonsubstituted monocyclic group or a substituted or nonsubstituted fused polycyclic group, or a combination of A and B or a combination of C and D is a heterocyclic ring including a nitrogen atom which bonds to an adjacent benzene ring.

According to the present invention, further, there is provided a light-emitting material for developing an organic EL device, which has the formula [2],

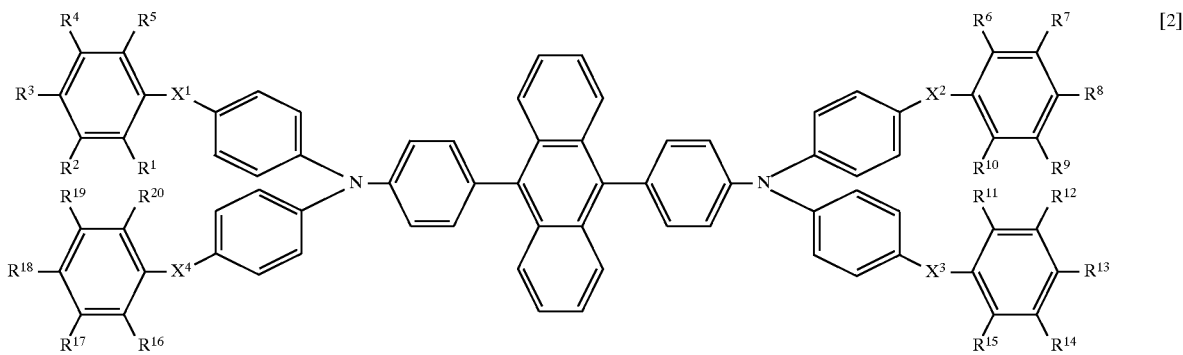

[2]

wherein each of $R^1$ to $R^{23}$ is independently a hydrogen atom, a halogen atom, a substituted or nonsubstituted alkyl group, a substituted or nonsubstituted alkoxy group, a substituted or nonsubstituted amino group, a substituted or nonsubstituted monocyclic group or a substituted or nonsubstituted fused polycyclic group, provided that adjacent substituents may form a saturated or unsaturated ring, and each of $X^1$ to $X^4$

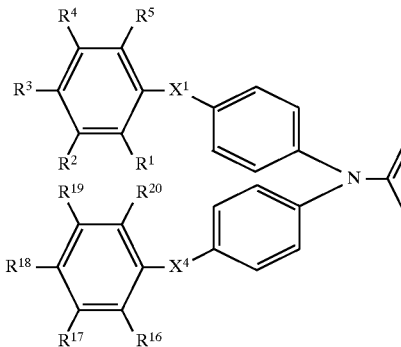

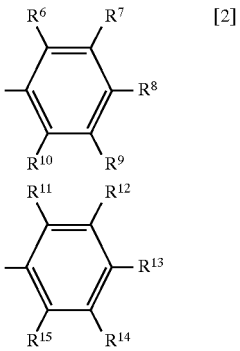 [2]

group, or a combination of A and B or a combination of C and D is a heterocyclic ring including a nitrogen atom which bonds to an adjacent benzene ring.

is independently a direct bond, O, S, C=O, $SO_2$, $(CH_2)_x$—O—$(CH_2)_y$, $(CH_2)_x$—S—$(CH_2)_y$, P, P=O, $SiR^{21}(R^{22})$, $NR^{23}$, a substituted or nonsubstituted alkylene group or a substituted or nonsubstituted aliphatic ring residue, provided that each of x and y is independently a positive integer of 0 to 20 while x+y=0 in no case.

Further, according to the present invention, there is provided an EL device obtained by forming a light-emitting layer or a plurality of thin organic compound layers including the light-emitting layer between an anode and a cathode, wherein the light-emitting layer contains the above light-emitting material.

DETAILED DESCRIPTION OF THE INVENTION

Figure 1:
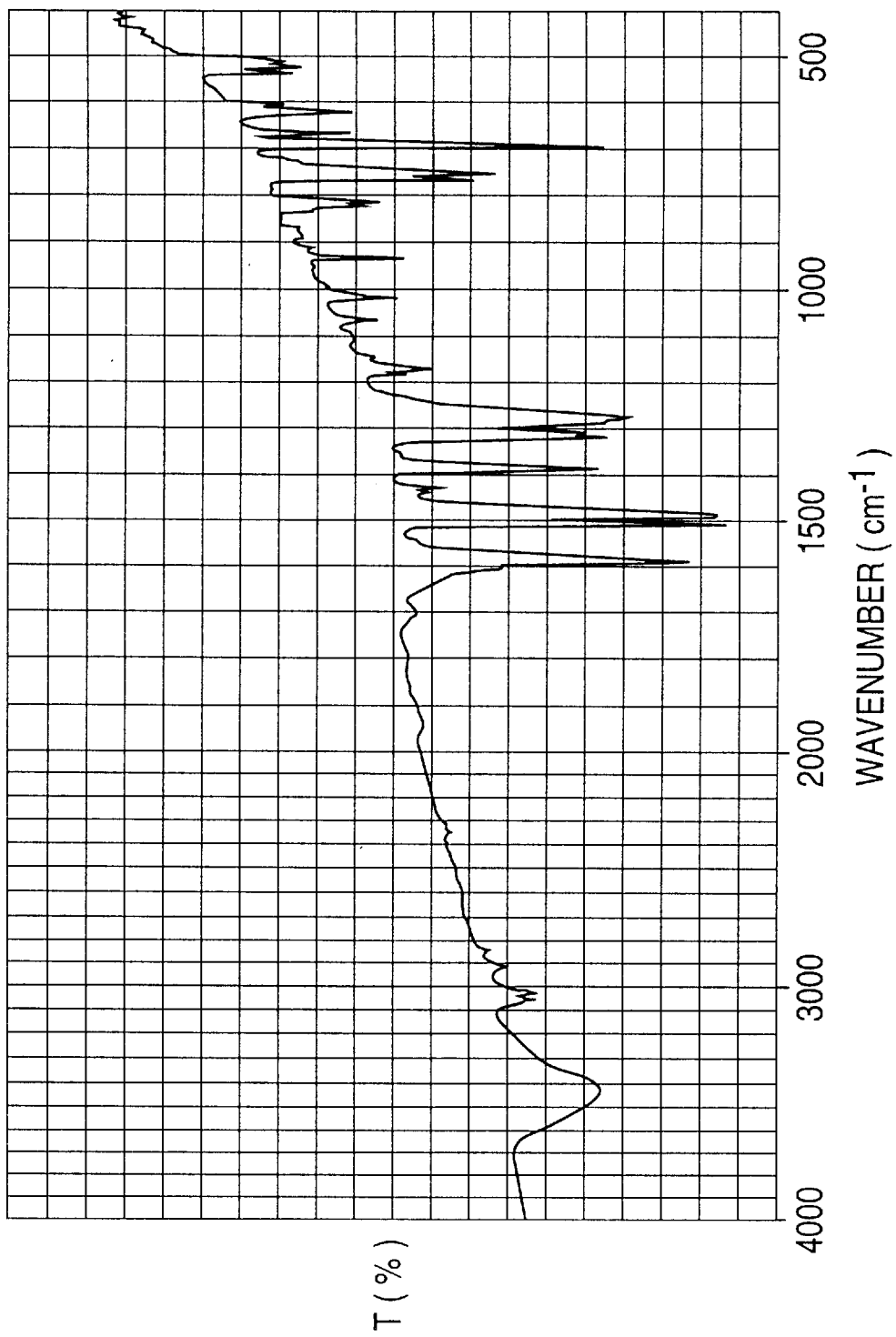
FIG. 1 is an infrared absorption spectrum of Compound (5).

The present inventors have made diligent studies and found that an organic EL device having a light-emitting layer for which the material of the formula [1] or [2] is adapted has a high light emission brightness and a long life of light emission, and on the basis of this finding, the present invention has been completed.

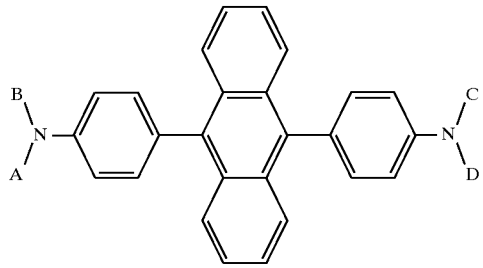

[1]

wherein each of A to D is a substituted or nonsubstituted alkyl group, a substituted or nonsubstituted monocyclic group or a substituted or nonsubstituted fused polycyclic wherein each of $R^1$ to $R^{23}$ is independently a hydrogen atom, a halogen atom, a substituted or nonsubstituted alkyl group, a substituted or nonsubstituted alkoxy group, a substituted or nonsubstituted amino group, a substituted or nonsubstituted monocyclic group or a substituted or nonsubstituted fused polycyclic group, provided that adjacent substituents may form a saturated or unsaturated ring, and each of $X^1$ to $X^4$ is independently a direct bond, O, S, C=O, $SO_2$, $(CH_2)_x$—O—$(CH_2)_y$, $(CH_2)_x$—S—$(CH_2)_y$, P, P=O, $SiR^{21}(R^{22})$, $NR^{23}$, a substituted or nonsubstituted alkylene group or a substituted or nonsubstituted aliphatic ring residue, provided that each of x and y is independently a positive integer of 0 to 20 while x+y=o in no case.

In the definitions of A to D in the formula [1] or in the definitions in the formula [2], the alkyl group includes linear or branched alkyl groups having 1 to 20 carbon atoms such as methyl, ethyl, propyl, butyl, sec-butyl, tert-butyl, pentyl, hexyl, heptyl, octyl and stearyl.

In the definitions in the formula [2], the alkylene includes linear or branched alkylene groups having 1 to 20 carbon atoms such as methylene, ethylene, propylene, butylene, sec-butylene, tert-butylene, pentylene, hexylene, heptylene, octylene and stearylene.

In the definitions of A to D in the formula [1] or in the definitions in the formula [2], the monocyclic group includes a monocyclic cycloalkyl group, a monocyclic aryl group and a monocyclic heterocyclic ring group.

The monocyclic cycloalkyl group includes cycloalkyl groups having 4 to 8 carbon atoms such as cyclobutyl, cyclopentyl, cyclohexyl, cycloheptyl and cyclooctyl.

The monocyclic aryl group includes phenyl.

The monocyclic heterocyclic ring group includes thionyl, thiophenyl, furanyl, pyrrolyl, imidazolyl, pyrazolyl, pyridyl, pyrazinyl, pyrimidyl, pyridiazinyl, oxazolyl, thizolyl, oxadiazolyl and thiadiazolyl.

In the definitions of A to D in the formula [1] or in the definitions in the formula [2], the fused polycyclic group includes a fused polycyclic aryl group and a fused polycyclic heterocyclic group and a fused cycloalkyl group.

The fused polycyclic aryl group includes naphthyl, anthranyl, phenanthrenyl, fluorenyl, acenaphthyl, azulenyl, heptanlenyl, acenaphthylenyl and pyrenyl.

The fused polycyclic heterocyclic ring includes indolyl, quinolyl, isoquinolyl, phthrazinyl, quinoxalinyl, quinazolinyl, carbozolyl, acridinyl, phenazinyl, furfuryl, isothiazolyl, isoxazolyl, furazanyl, phenoxazinyl, benzoxazolyl, benzothiazolyl and benzoimidazolyl.

Examples of the substituent on the above alkyl, the above monocyclic group, the above fused polycyclic group or the heterocyclic ring which is formed by the combination of A and B or the combination of C and D and includes a nitrogen atom which bonds to an adjacent benzene ring, and $R^1$ and $R^{20}$ in the formula [2] are as follows.

Halogen atoms such as fluorine, chlorine, bromine and iodine.

Substituted or nonsubstituted alkyl groups such as methyl, ethyl, propyl, butyl, sec-butyl, tert-butyl, pentyl, hexyl, heptyl, octyl, stearyl, trichloromethyl, trifluoromethyl, cyclopropyl, cyclohexyl, 1,3-cyclohexadienyl, 2-cyclopenten-1-yl, 2,4-cyclopentadien-1-ylidenyl, benzyl, dimethylbenzyl and di(trifluoromethyl)benzyl.

Substituted or nonsubstituted alkoxy groups such as methoxy, ethoxy, propoxy, n-butoxy, tert-butoxy, pentyloxy, hexyloxy, stearyloxy and trifluoromethoxy.

Substituted or nonsubstituted thioalkoxy groups such as methylthio, ethylthio, propylthio, butylthio, sec-butylthio, tert-butylthio, pentylthio, hexylthio, heptylthio and octylthio.

Mono- or di-substituted amino groups such as methylamino, diemthylamino, ethylamino, diethylamino, dipropylamino, dibutylamino, phenylmethylamino, diphenylamino, ditolylamino, dibenzylamino, bis(acetoxymethyl)amino, bis(acetoxyethylamino) and bis(acetoxypropylamino).

Substituted or nonsubstituted aryloxy groups such as phenoxy, p-tert-butylphenoxy and 4-methylphenoxy.

Substituted or nonsubstituted arylthio groups such as phenylthio and 4-methylphenylthio.

Substituted or nonsubstituted aryl groups such as phenyl, biphenyl, terphenyl, 4-methylthiphenyl, 3,5-dicyanophenyl, o-, m- or p-tolyl, xylyl, benzylphenyl, dimethylbenzylphenyl, o-, m- or p-cumenyl, mesityl, pentalenyl, indenyl, naphthyl, azulenyl, heptalenyl, acenaphthylenyl, phenanthrenyl, fluorenyl, anthryl, anthraquinolyl, 3-methylanthryl, triphenylenyl, pyrenyl, chrysenyl, picenyl, perylenyl, pentaphenyl, pentacenyl, tetraphenylenyl, hexaphenyl, hexacenyl, rubicenyl, coronenyl, trinaphthylenyl, heptaphenyl, heptacenyl, pyranthrenyl and ovalenyl.

Substituted or nonsubstituted heterocyclic ring groups such as thionyl, thiphenyl, furanyl, pyrrolyl, imidazolyl, pyrazolyl, pyridyl, pyrazinyl, pyrimidyl, pyridiazinyl, isoindolyl, quinolyl, isoquinolyl, phthlazinyl, quinoxalinyl, quinazolinyl, carbozolyl, acridinyl, phenazinyl, furfuryl, isothiazolyl, isoxazolyl, furazanyl, phenoxazinyl, benzoxazolyl, benzothiazolyl, benzoimidazolyl, 2-methylpyridyl, 3-cyanopyridyl, oxazolyl, thiazolyl, oxadiazolyl, thiadiazolyl and imidazolyl.

The compound of the formula [1] or [2], which has a substituent having an aromatic ring or which has substituents forming an aromatic ring, has a high glass transition temperature and a high melting point, and it therefore gives an organic EL device having a high light emission brightness when used as a light-emitting material for an organic EL device, and has an advantage in the durability against the deterioration of the device under Joule's heat when the organic EL device is used for light emission for a long period of time.

The compound of the formula [1] or [2], provided by the present invention, is synthesized, for example, by the following method.

9,10-Bis(4-halogenophenyl)anthracene and a diamine derivative which may have a substituent, or 9,10-bis(4-aminophenyl)anthracene and a halogenated derivative which may have a substituent are allowed to react in a solvent in the presence of a base and a catalyst. The above anthracene derivative may be replaced with an anthraquinone derivative. The base is selected from potassium carbonate, sodium carbonate, potassium hydroxide, sodium hydroxide or aqueous ammonia. The catalyst is selected from a copper powder, cuprous chloride, tin, stannous chloride, pyridine, aluminum trichloride or titanium tetrachloride. The solvent is selected from any solvents having high boiling points such as nitrobenzene, dimethylformamide, 1,3-dimethyl-2-imidazolidinone, benzene, toluene and xylene.

The following Table 1 specifically shows typical examples of the compound of the present invention, while the present invention shall not be limited to these compounds.

TABLE 1

| Compound | Chemical structure |
|---|---|
| (1) | 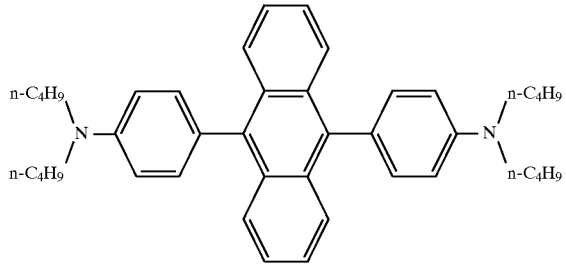 |

TABLE 1-continued
| Compound | Chemical structure |
| --- | --- |
| (2) | 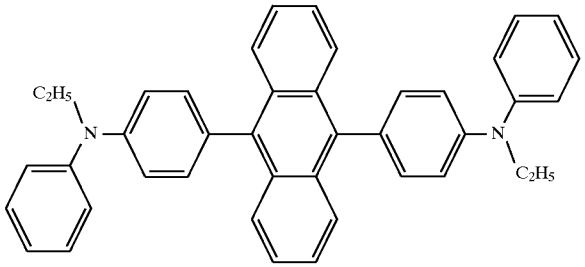 |
| (3) | 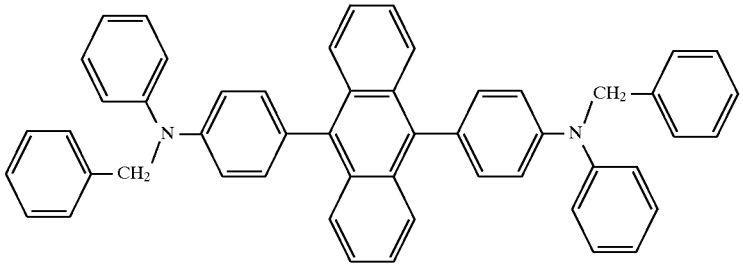 |
| (4) | 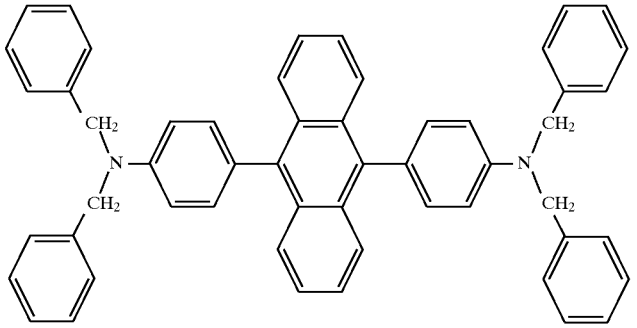 |
| (5) | 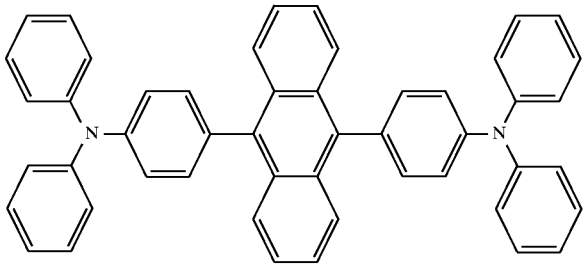 |
| (6) | 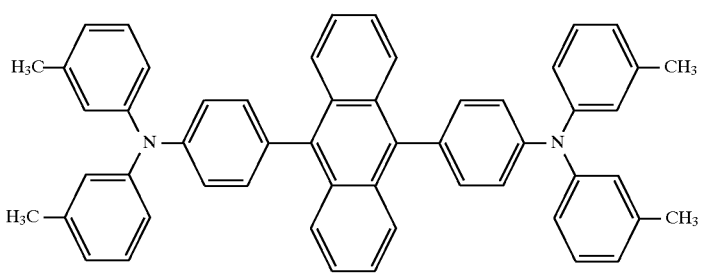 |

TABLE 1-continued
| Compound | Chemical structure |
|---|---|
| (7) | 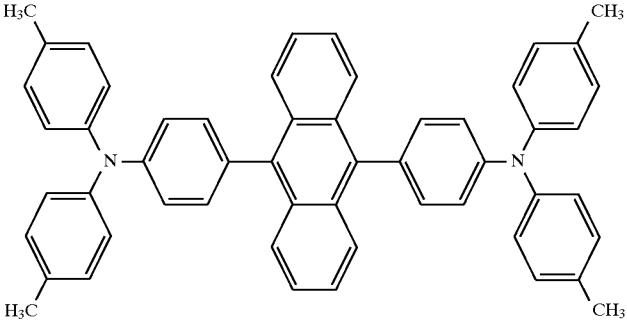 |
| (8) | 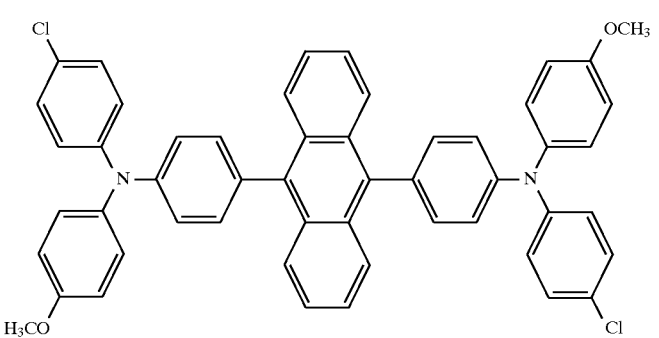 |
| (9) | 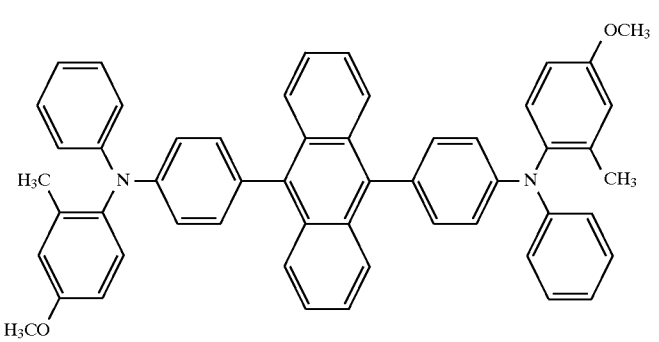 |
| (10) | 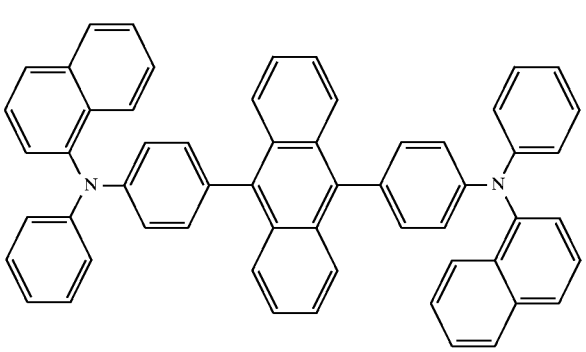 |

TABLE 1-continued
| Compound | Chemical structure |
|---|---|
| (11) | 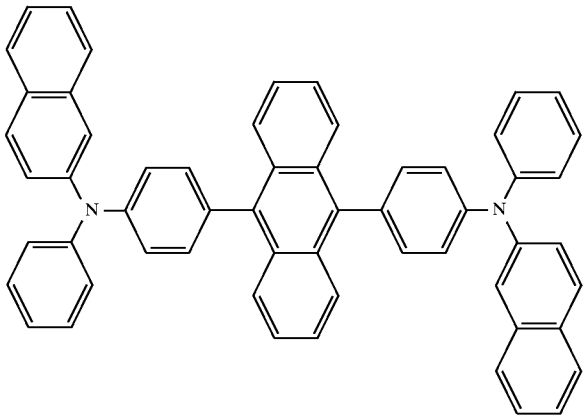 |
| (12) | 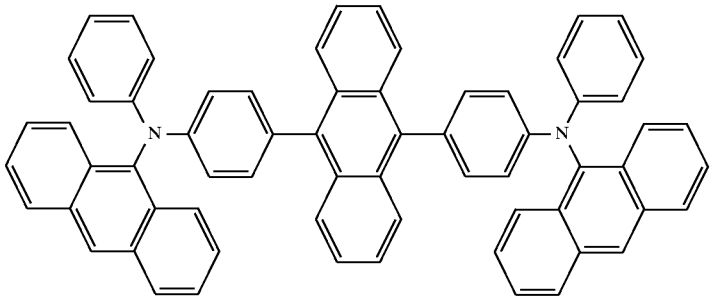 |
| (13) | 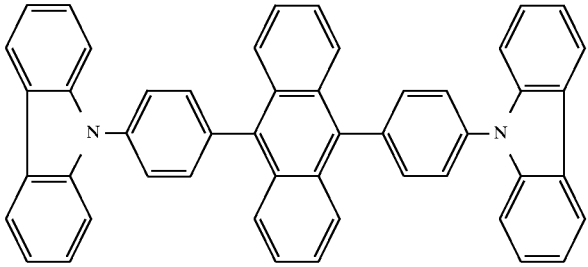 |
| (14) | 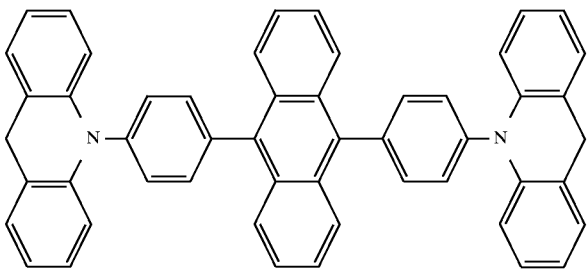 |
| (15) | 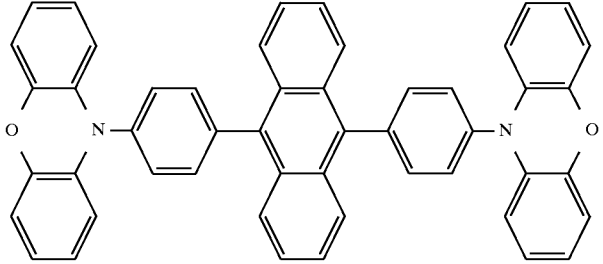 |

TABLE 1-continued

| Compound | Chemical structure |
|---|---|
| (16) | 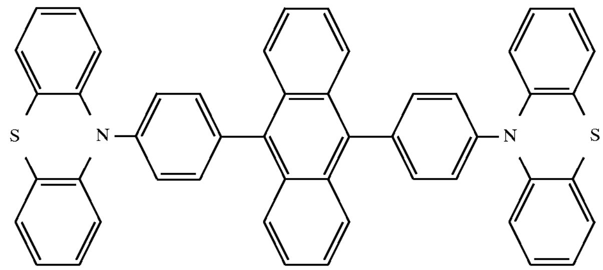 |
| (17) | 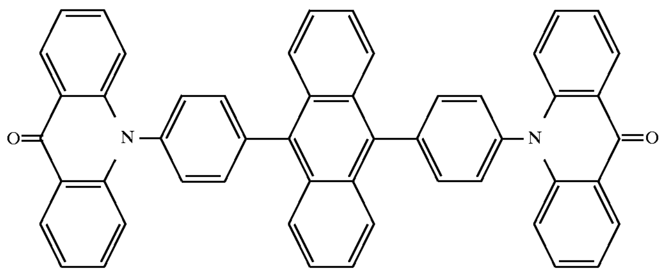 |
| (18) | 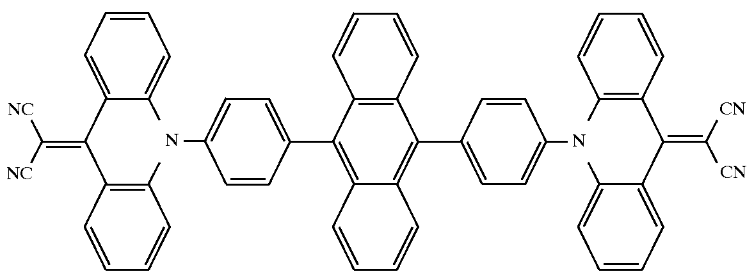 |
| (19) | 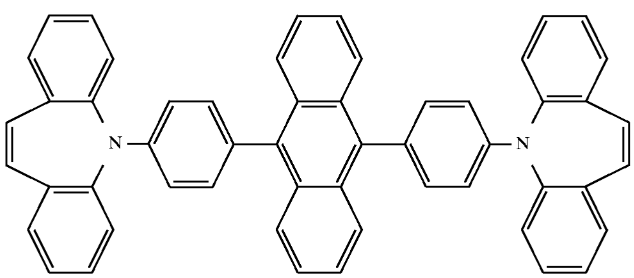 |
| (20) | 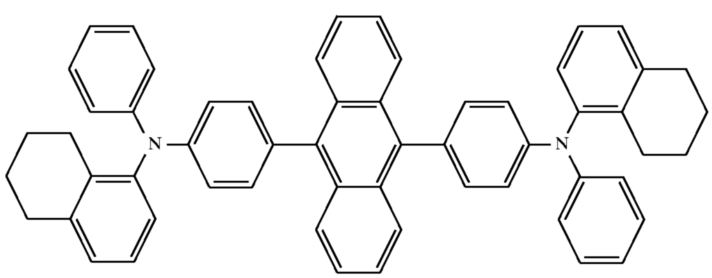 |

TABLE 1-continued

| Compound | Chemical structure |
| --- | --- |
| (21) | 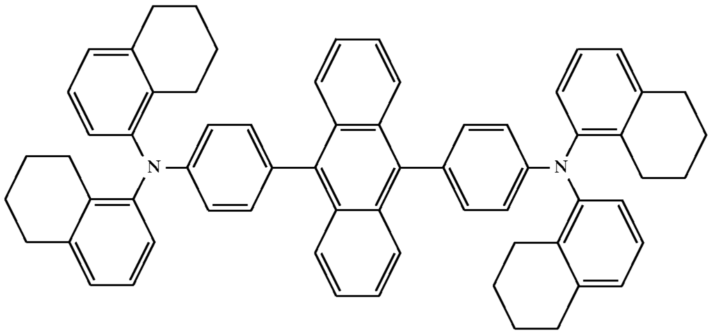 |
| (22) | 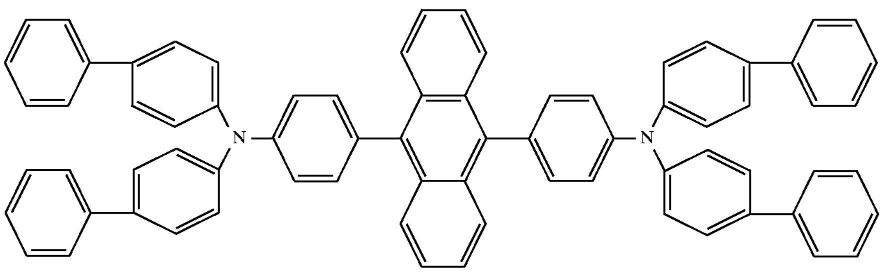 |
| (23) | 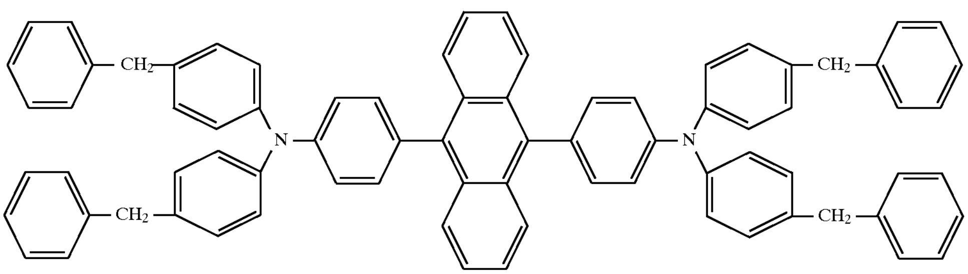 |
| (24) | 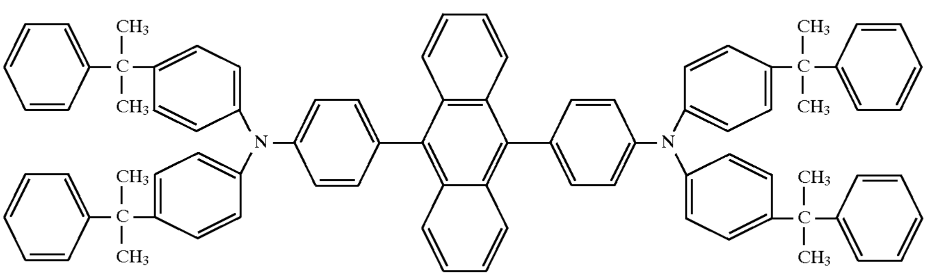 |
| (25) | 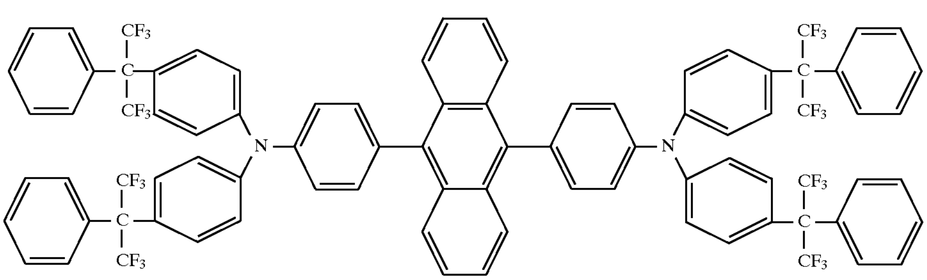 |

TABLE 1-continued
| Compound | Chemical structure |
|---|---|
| (26) | 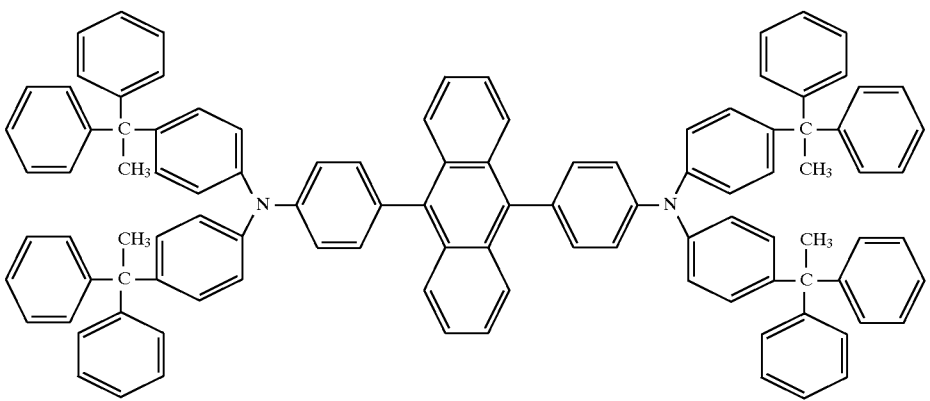 |
| (27) | 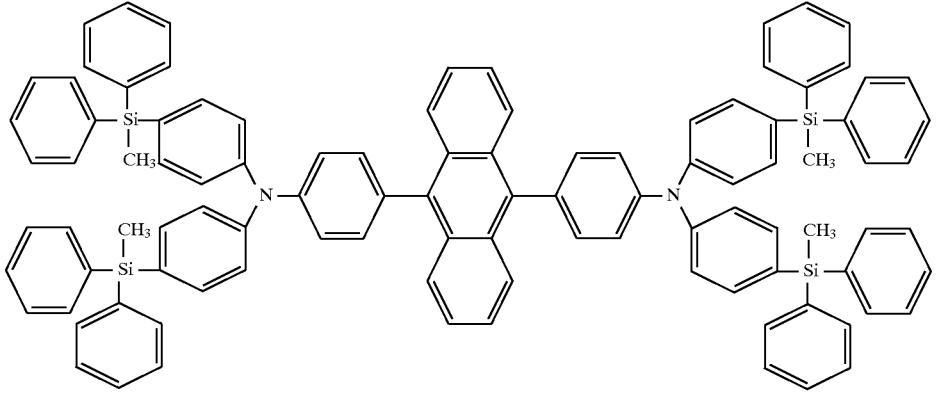 |
| (28) | 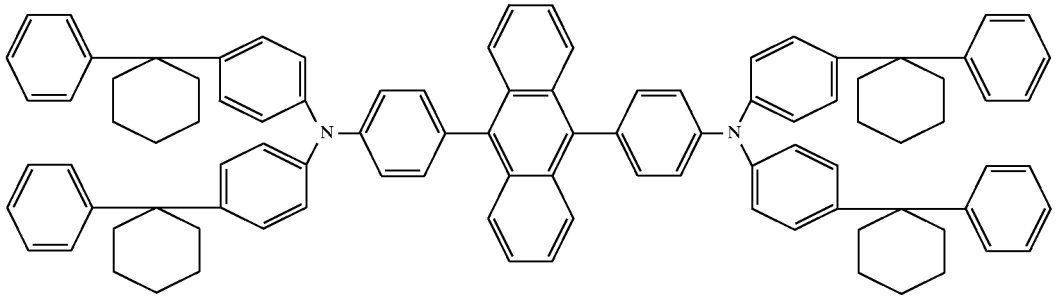 |
| (29) | 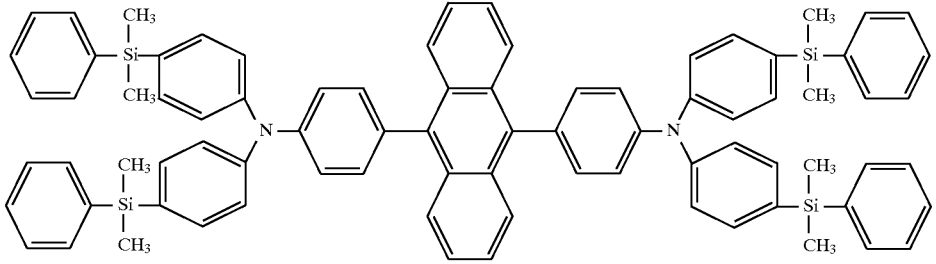 |

TABLE 1-continued
| Compound | Chemical structure |
|---|---|
| (30) | 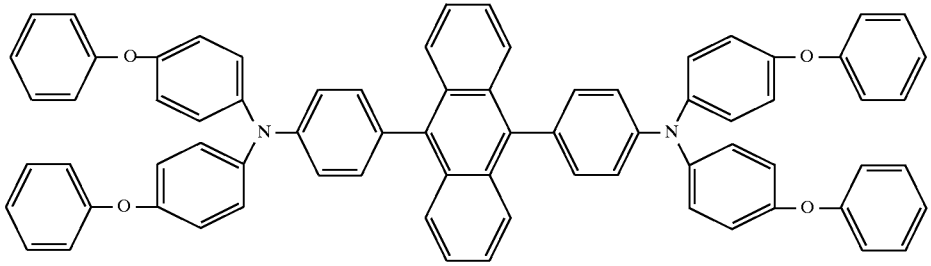 |
| (31) | 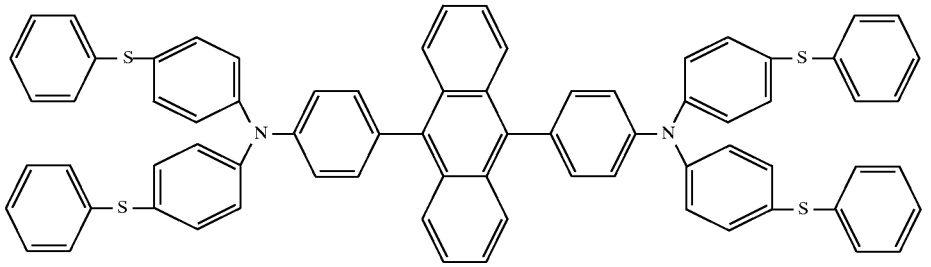 |
| (32) | 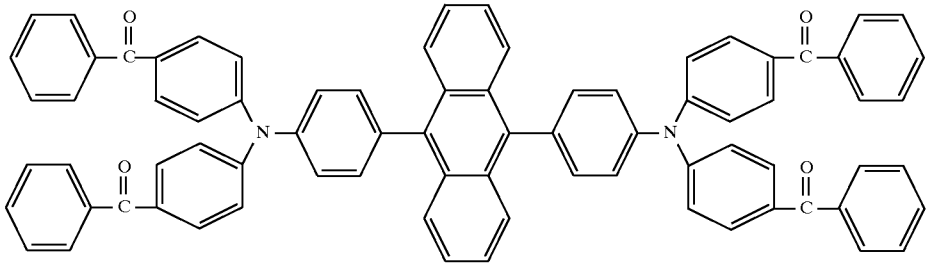 |
| (33) | 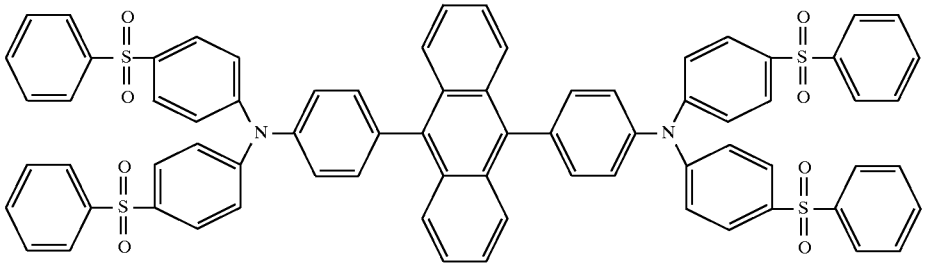 |
| (34) | 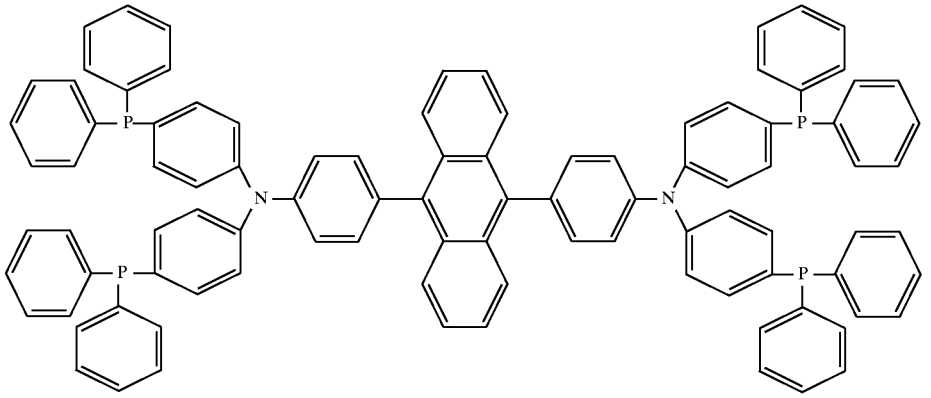 |

TABLE 1-continued

| Compound | Chemical structure |
|---|---|
| (35) | 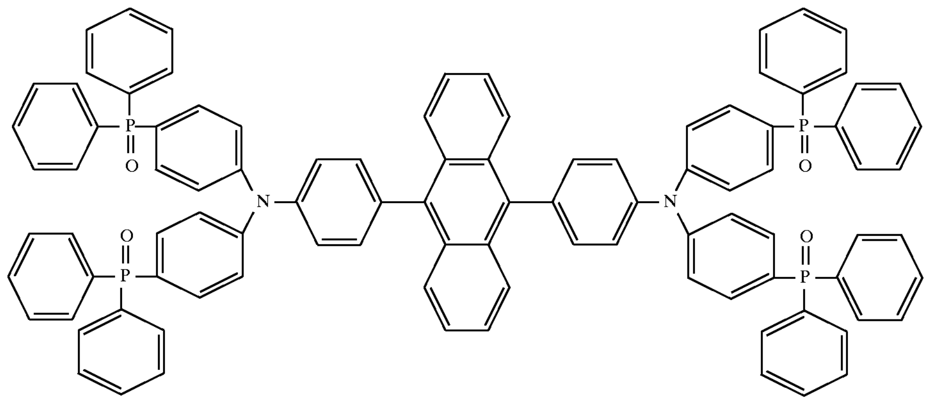 |
| (36) | 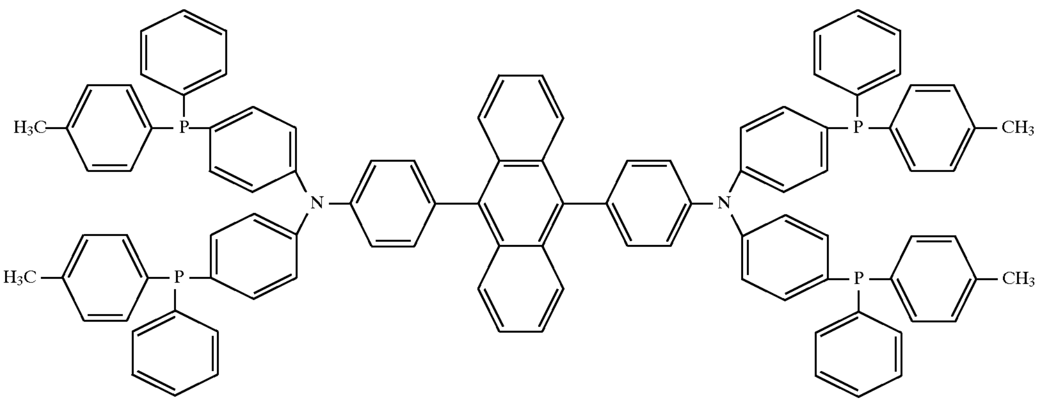 |
| (37) | 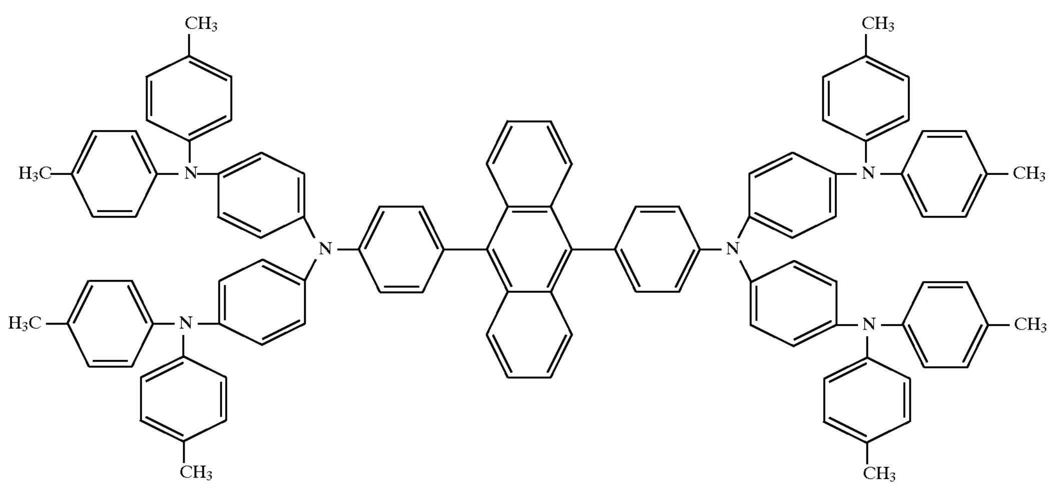 |
| (38) | 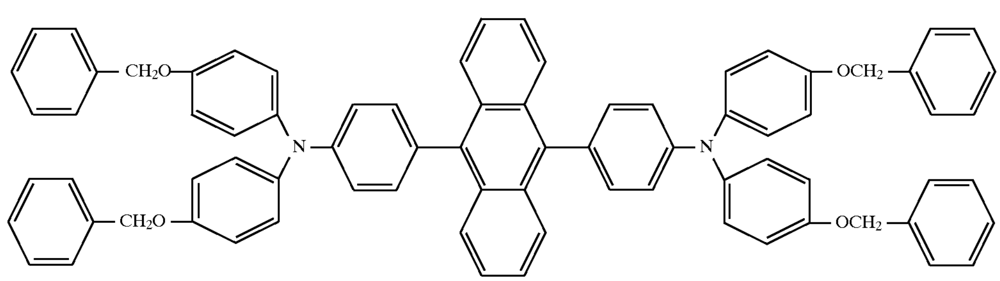 |

TABLE 1-continued

| Compound | Chemical structure |
| --- | --- |
| (39) | 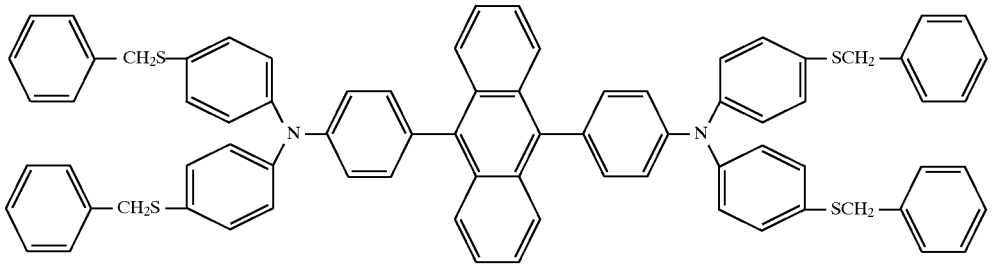 |
| (40) | 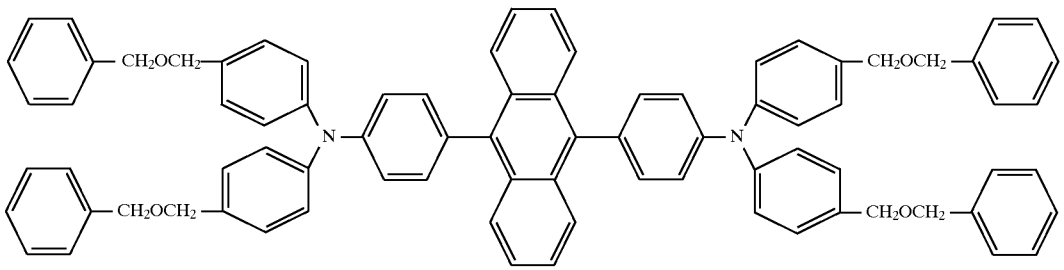 |

The compound of the formula [1] or [2] in the present invention does not show much decrease in light emission density in a solid state, and it is stable when a field is applied. It is therefore excellent as a light-emitting material for a field-emission type device. Further, the compound of the formula [1] or [2] is highly capable of receiving holes, and therefore, it can be also used as a hole-transporting type light-emitting material. Further, the light-emitting layer formed of the compound of the formula [1] or [2] may contain other hole-injecting material, electron-injecting material, light-emitting material or dopant.

The organic EL device has a structure in which a mono- or multi-layered organic thin film is formed between an anode and a cathode. In a mono-layered device, a light-emitting layer is formed between the anode and the cathode. The light-emitting layer contains a light-emitting material, and in addition thereto, it may contain a hole-transporting material for transporting holes injected from the anode to the light-emitting material, or an electron-transporting material for transporting electrons injected from the cathode to the light-emitting material. In a multi-layered device, the organic EL device has one of laminated-layer structures, for example, of (anode/hole-injecting layer/light-emitting layer/ cathode), (anode/light-emitting layer/electron-injecting layer/cathode) and (anode/hole-injecting layer/light-emitting layer/electron-injecting layer/cathode). The compound of the formula [1] or [2] can be used as an effective light-emitting material in the light-emitting layer.

The light-emitting layer may contain other light-emitting material, a dopant, a hole-injecting material and an electron-injecting material as required in addition to the compound of the formula [1] or [2]. The above multi-layer structure of the organic EL device can serve to prevent quenching-induced decreases in the brightness and the device life. In the above multi-layered device, a light-emitting material, a dopant, a hole-transporting material for transporting a carrier and an electron-transporting material may be used in combination as required. Further, some dopants improve the device in light emission brightness and light emission efficiency and serve to give the light emission in a color of from blue to red. Further, each of the hole-injecting layer, the light-emitting layer and the electron-injecting layer may have the structure of at least two layers.

The electrically conductive material used for the anode of the organic EL device is suitably selected from those materials having a work function of greater than 4 eV. This electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electrically conductive resins such as polythiophene and polypyrrole.

The electrically conductive material used for the cathode is suitably selected from those having a work function of smaller than 4 eV. This electrically conductive material includes magnesium, calcium, tin, lead, titanium, yttrium, lithium, ruthenium, manganese, and alloys of these. Typical examples of the alloys include magnesium/silver, magnesium/indium and lithium/aluminum, while the alloys shall not be limited to these. Each of the anode and the cathode may be formed of two layers or more as required.

For the effective light emission of the organic EL device, at least one of the electrodes is desirably transparent in the light emission wavelength region of the device. Further, the substrate is desirably transparent. The transparent electrode is produced from the above electrically conductive material by a deposition method or a sputtering method such that a predetermined transparency is secured. The electrode which forms a light emission surface preferably has a light transmittance of at least 10%. The substrate is not specially limited if it has adequate mechanical and thermal strength and is transparent. For example, it is selected from glass substrates and substrates of transparent resins such as a polyethylene substrate, a polyethylene terephthalate substrate, a polyether sulfone substrate and a polypropylene substrate.

Each of the layers forming the organic EL device of the present invention can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. Generally, the thickness of each layer is preferably in the range of from 5 nm to 10 $\mu$m, more preferably 10 nm to 0.2 $\mu$m.

In the wet film forming method, a material for forming an intended layer is dissolved or dispersed in a proper solvent, and a thin film is formed from the solution or dispersion. The solvent is selected from ethanol, chloroform, tetrahydrofuran and dioxane, while the solvent shall not be limited to these. For improving the film formability and preventing the occurrence of pinholes, the above solution or dispersion for forming the layer may contain a proper resin and a proper additive. The resin suitable for use in the present invention includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electrically conductive resins such as polythiophene and polypyrrole. The above additive includes an antioxidant, an ultraviolet absorbent and a plasticizer.

In the organic EL device of the present invention may contain, the light-emitting layer, the hole-injecting layer and the electron-injecting layer may contain a known light-emitting material, a known dopant, a known hole-injecting material or a known electron-injecting material.

The light-emitting material or the dopant which may be used in the light-emitting layer together with the compound of the formula [1] or [2] includes anthracene, naphthalene, phenanthrene, pyrene, tetracene, coronene, chrysene, fluorescein, perylene, phthaloperylene, naphthaloperylene, perinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, benzidine type tiphenylamine, styrylamine type triphenylamine, diamine type triphenylamine and known fluorescent dyestuffs, although the above material shall not be limited to these.

The hole-injecting material is selected from compounds which are capable of transporting holes, have an effect on receiving holes from the anode, have an excellent effect of injecting holes to the light-emitting layer or the light-emitting material, prevent the movement of excitons generated in the light-emitting layer to the electron-injecting layer or the electron-injecting material and have the excellent capability of forming a thin film. Specific examples of the above hole-injecting material include a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electrically conductive polymer. However, the hole-transporting material shall not be limited to the above materials.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyldiphenylamine, N,N'-diphenyl-N,N'-(3-methylphenyl)-1,1-biphenyl-4,4'-diamine, N,N-N',N'-(4-methylphenyl)-1,1'-phenyl-4,4'-diamine, N,N-N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenylcyclohexane, and origomers or polymers having aromatic tertiary amine structures of these. Although no specially limited, specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc.

The electron-injecting material is a material which is capable of transporting electrons, receiving electrons from the cathode, injecting electrons into the light-emitting layer or light-emitting material, preventing excitons generated in the light-emitting layer from moving into the hole-injecting layer and forming a thin film. Although not specially limited, examples of the electron-injecting material include fluorenone, anthraquinodimethane, diphenoquinone, thiopyran dioxide, oxazole, oxadiazole, triazole, imidazole, perylenetetracarboxylic acid, fluorenylidenemethane, anthraquinodimethane, anthrone, a metal complex and derivatives of these. The hole-injecting material may be sensitivity-increased by incorporating an electron-accepting material, and the electron-injecting material may be sensitivity-increased by incorporating an electron-donating material.

In the organic EL device of the present invention, the electron-injecting material which is more effective is a metal complex compound or a nitrogen-containing five-membered derivative. Although not specially limited, specific examples of the metal complex compound include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), and gallium bis(2-methyl-8-quinolinate)(2-naphtholate). The nitrogen-containing five-membered derivative is preferably oxazole, thiazole, thiadiazole, or a triazole derivative. Although not specially limited, specific examples of the above nitrogen-containing five-membered derivative include 2,5-bis(1-phenyl)-1,3,4-oxazole, dimethyl POPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene.

In the organic EL device of the present invention, the layer containing the compound of the formula [1] or [2] may contain at least one of the light-emitting material, the dopant, the hole-injecting material and the electron-injecting material. For improving the organic EL device of the present invention in the durability against temperature, humidity and ambient atmosphere, a protective layer may be formed on the surface of the device, or the device as a whole may be sealed with a silicone oil, or the like.

As explained above, the present invention can increase the light emission efficiency and the light emission brightness owing to the use of the compound of the formula [1] or [2] in the organic EL device. Further, the organic EL device of the present invention is highly stable against heat and electric current and can provide a practically acceptable light emission brightness at a low drive voltage, and the device can be greatly improved with regard to the deterioration of the brightness, a large problem of a conventional evice.

The organic EL device of the present invention has high industrial values since it can be adapted for a flat panel display of an on-wall television set, a flat light-emitting device, a light source for a copying machine or a printer, a light source for a liquid crystal display or counter, a display signboard and a signal light.

The material of the present invention can be used in the fields of an organic EL device, an electrophotographic photoreceptor, a photoelectric converter, a solar cell, an image sensor, and the like.

EXAMPLES

The present invention will be explained more in detail with reference to Examples hereinafter, in which "part" stands for "part by weight".

Synthesis Examples

Synthesis of Compound (3)

7.9 Parts of 9,10-bis(4-bromophenyl)anthracene, 5.5 parts of N-phenylbenzylamine, 4 parts of potassium carbonate and 0.5 part of a copper powder were added to 30 parts of nitrobenzene, and the mixture was stirred in a nitrogen atmosphere at 205° C. for 15 hours. Then, a formed brown solid wax extracted with toluene, concentrated and purified by silica gel column chromatography, and the purified product was recrystallized from n-hexane to give 3.8 parts of a powder having the fluorescence of a yellowish green color. The powder was analyzed for a molecular weight to show that it was Compound (3).

The result of elemental analysis of the formed product was as follows.

Result of Elemental Analysis As $C_{52}H_{40}N_2$

Calculated (%): C: 90.14, H: 5.82, N: 4.04

Found (%): C: 90.26, H: 5.95, N: 3.79

Synthesis of Compound (5)

18 Parts of 9,10-bis (4-aminophenyl)anthracene, 100 parts of iodobenzene, 0.5 part of cuprous chloride and 22 parts of potassium hydroxide were added to 100 parts of 1,3-dimethyl-2-imidazolidinone, and the mixture was stirred at 205° C. for 30 hours. Then, the reaction mixture was diluted with 500 parts of water, a formed wax collected by filtration and washed with water. Then, the product was extracted with toluene, concentrated and purified by silica gel column chromatography to give 21 parts of a powder having the fluorescence of a blue color. The powder was analyzed for a molecular weight to show that it was Compound (5).

The result of elemental analysis of the formed product was as follows.

Result of Elemental Analysis As $C_{50}H_{36}N_2$

Calculated (%): C: 90.37, H: 5.42, N: 4.21

Found (%): C: 90.49, H: 5.53, N: 3.98

FIG. 1 shows the infrared absorption spectrum (KBr tablet method) of the above compound.

Synthesis of Compound (6)

15 Parts of 9,10-bis(4-aminophenyl)anthracene, 150 parts of m-iodotoluene, 0.5 part of cuprous chloride and 20 parts of potassium hydroxide were added to 50 parts of 1,3-dimethyl-2-imidazolidinone, and the mixture was stirred at 205° C. for 30 hours. Then, the reaction mixture was diluted with 500 parts of water, a formed wax collected by filtration and washed with water. Then, the product was extracted with toluene, concentrated and purified by silica gel column chromatography to give 25 parts of a powder having the fluorescence of a blue color. The powder was analyzed for a molecular weight to show that it was Compound (6).

The result of elemental analysis of the formed product was as follows.

Result of Elemental Analysis As $C_{54}H_{44}N_2$

Calculated (%): C: 89.96, H: 6.15, N: 3.89

Found (%): C: 90.05, H: 6.21, N: 3.74

Figure 2:
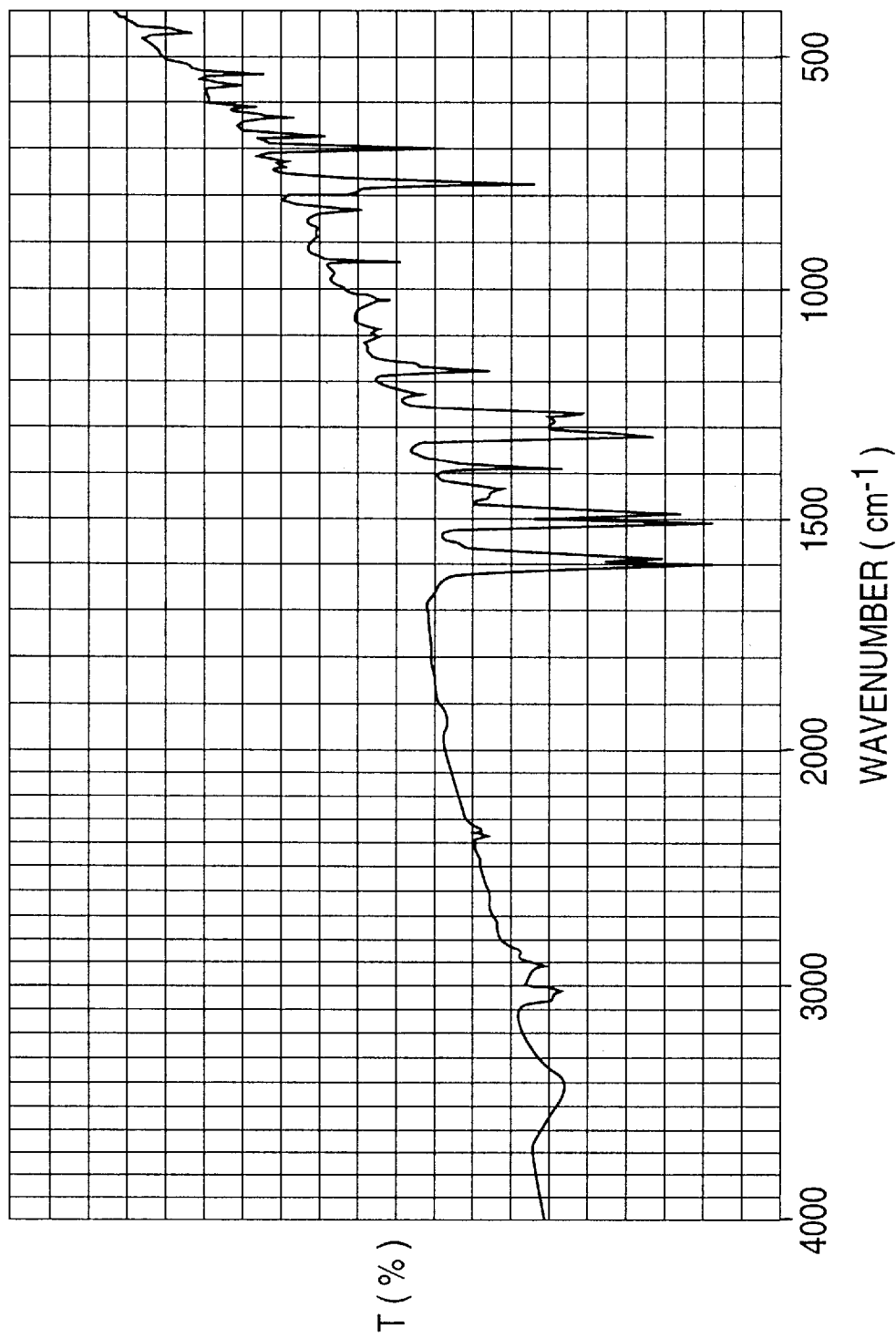
FIG. 2 is an infrared absorption spectrum of Compound (6).

FIG. 2 shows the infrared absorption spectrum (KBr tablet method) of the above compound.

Synthesis of Compound (7)

8.9 Parts of 9,10-bis(4-iodophenyl)anthracene, 5.9 parts of 4,4,-dimethyldiphenylamine, 4 parts of potassium carbonate and 0.5 part of a copper powder were added to 20 parts of nitrobenzene, and the mixture was stirred in a nitrogen atmosphere at 205° C. for 10 hours. Then, a formed brown solid wax extracted with toluene, concentrated and purified by silica gel column chromatography, and the purified product was recrystallized from n-hexane to give 3.5 parts of a powder having the fluorescence of a bluish green color. The powder was analyzed for a molecular weight to show that it was Compound (7).

The result of elemental analysis of the formed product was as follows.

Result of Elemental Analysis As $C_{54}H_{44}N_2$

Calculated (%): C: 89.96, H: 6.15, N: 3.89

Found (%): C: 89.90, H: 6.23, N: 3.87

Figure 3:
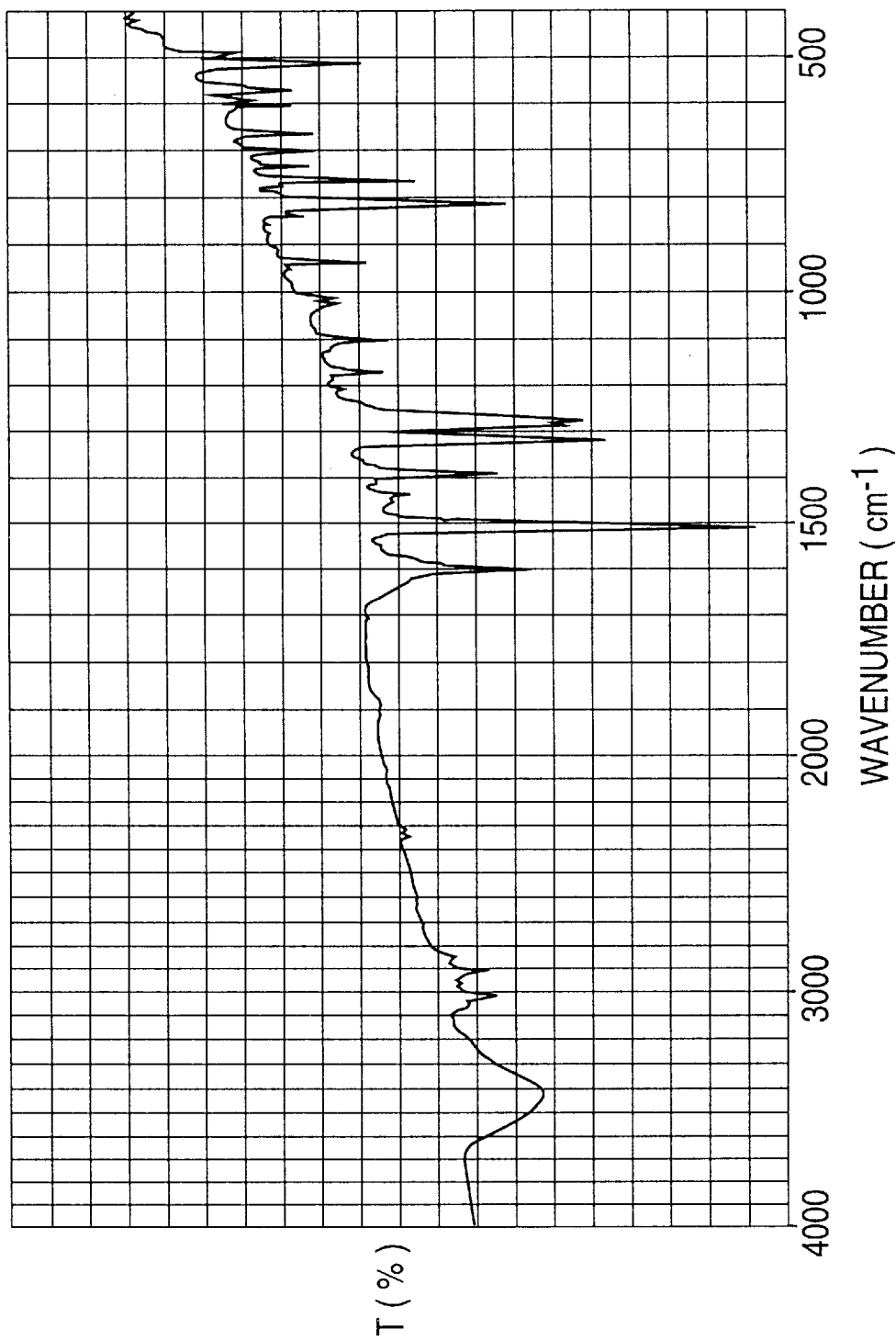
FIG. 3 is an infrared absorption spectrum of Compound (7).

FIG. 3 shows the infrared absorption spectrum (KBr tablet method) of the above compound.

Synthesis of Compound (24)

8.9 Parts of 9,10-bis(4-iodophenyl)anthracene, 12.2 parts of 4,4,-diisopropyl(2-phenyl)diphenylamine, 4 parts of potassium carbonate and 0.5 part of a copper powder were added to 30 parts of nitrobenzene, and the mixture was stirred in a nitrogen atmosphere at 205° C. for 15 hours. Then, a formed brown solid wax extracted with toluene, concentrated and purified by silica gel column chromatography, and the purified product was recrystallized from n-hexane to give 4.8 parts of a powder having the fluorescence of a yellowish green color. The powder was analyzed for a molecular weight to show that it was Compound (24).

The result of elemental analysis of the formed product was as follows.

Result of Elemental Analysis As $C_{86}H_{76}N_2$

Calculated (%): C: 90.81, H: 6.73, N: 2.46
Found (%): C: 90.95, H: 6.82, N: 2.77

Example 1

Compound (7), 2,5-bis(1-naphthyl)-1,3,4-oxadiazole and a polycarbonate resin (Panlite K-1300, supplied by Teijin Chemical Ltd.) in a Compound (7)/oxadiazole/polycarbonate resin weight ratio of 2/3/5 were dissolved in tetrahydrofuran, and the resultant solution was coated on a cleaned glass substrate with an ITO electrode by a spin coating method to form a light-emitting layer having a thickness of 100 nm. An electrode having a thickness of 150 nm was formed thereon from a magnesium/silver alloy having a magnesium/silver mixing ratio of 10/1, to obtain an organic EL device. The organic EL device showed a blue light emission having a brightness of 90 (cd/m$^2$) at a direct current voltage of 5 V, a maximum light emission brightness of 7,500 (cd/m$^2$) and a light emission efficiency of 0.7 (lm/W).

Example 2

Compound (9) was dissolved in methylene chloride, and the resultant solution was coated on a cleaned glass substrate with an ITO electrode by a spin coating method to form a light-emitting layer having a thickness of 50 nm. Then, a tris(8-hydroxyquinolinate)aluminum complex (Alq3) was vacuum-deposited on the light-emitting layer to form an electron-injecting layer having a thickness of 30 nm. An electrode having a thickness of 100 nm was formed thereon from a magnesium/silver alloy having a magnesium/silver mixing ratio of 10/1, to obtain an organic EL device. A hole-injecting layer and the light-emitting layer were deposited under vacuum at 10$^{-6}$ Torr at a substrate temperature of room temperature. The organic EL device showed a blue light emission having a brightness of 200 (cd/n$^2$) at a direct current voltage of 5 V, a maximum light emission brightness of 13,000 (cd/m$^2$) and a light emission efficiency of 1.2 (lm/W).

Example 3

Compound (41) having the following chemical structure was vacuum-deposited on a cleaned glass plate with an ITO electrode to form a hole-injecting layer having a thickness of 40 mm. Then, Compound (24) was vacuum-deposited to form a light-emitting layer having a thickness of 40 nm, and further, Alq3 was vacuum-deposited to form an electron-injecting layer having a thickness of 40 nm. An electrode having a thickness of 100 nm was formed thereon from a magnesium/silver alloy having a magnesium/silver mixing ratio of 10/1, to obtain an organic EL device. Each layer was deposited under vacuum at 10$^{-6}$ Torr at a substrate temperature of room temperature. The organic EL device showed a blue light emission having a brightness of 380 (cd/m$^2$) at a direct current voltage of 5 V, a maximum light emission brightness of 18,500 (cd/m$^2$) and a light emission efficiency of 1.9 (lm/W).

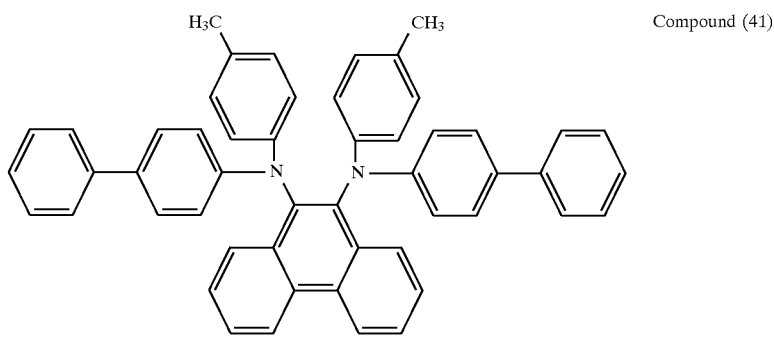

Compound (41)

Examples 4–43

Compound (42) having the following chemical structure was vacuum-deposited on a cleaned glass substrate with an ITO electrode to form a hole-injecting layer having a thickness of 40 nm. Then, Compound shown in Table 2 as a light-emitting material was vacuum-deposited to form a light-emitting layer having a thickness of 40 nm. Further, Compound (43) having the following chemical structure was vacuum-deposited to form an electron-injecting layer having a thickness of 40 nm. An electrode having a thickness of 150 nm was formed thereon from a magnesium/silver alloy having a magnesium/silver mixing ratio of 10/1, to obtain an organic EL device. Each layer was deposited under vacuum at 10$^{-6}$ Torr at a substrate temperature of room temperature. Table 2 shows the light emission characteristics of organic EL devices obtained in the above manner. Each value of light emission brightness was obtained at a direct current voltage of 5 V. All the organic EL devices obtained in these Examples showed blue light emission with a high light emission efficiency.

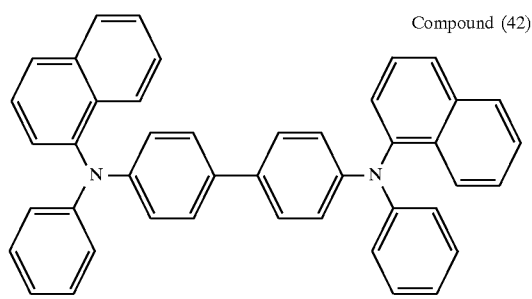

Compound (42)

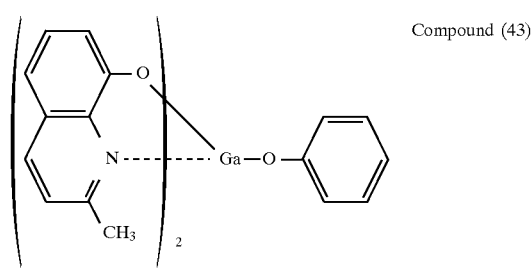

Compound (43)

TABLE 2

| Example | Compound | Light emission brightness (cd/m$^2$) | Maximum light emission brightness (cd/m$^2$) | Light emission efficiency (lm/W) |
|---|---|---|---|---|
| 4 | (1) | 490 | 21,000 | 2.2 |
| 5 | (2) | 510 | 22,000 | 2.2 |
| 6 | (3) | 600 | 31,000 | 3.1 |
| 7 | (4) | 590 | 29,000 | 2.9 |
| 8 | (5) | 620 | 33,000 | 3.3 |
| 9 | (6) | 650 | 30,000 | 3.5 |
| 10 | (7) | 880 | 35,000 | 4.2 |
| 11 | (8) | 660 | 31,000 | 3.2 |
| 12 | (9) | 730 | 31,000 | 3.0 |
| 13 | (10) | 810 | 34,000 | 3.8 |
| 14 | (11) | 780 | 30,000 | 3.5 |
| 15 | (12) | 800 | 33,000 | 3.4 |
| 16 | (13) | 770 | 41,000 | 3.0 |
| 17 | (14) | 720 | 37,000 | 2.9 |
| 18 | (15) | 740 | 36,000 | 3.0 |
| 19 | (16) | 750 | 33,000 | 2.8 |
| 20 | (17) | 730 | 34,000 | 3.0 |
| 21 | (18) | 680 | 29,000 | 2.8 |
| 22 | (19) | 800 | 39,000 | 3.8 |
| 23 | (20) | 780 | 37,000 | 3.7 |
| 24 | (21) | 770 | 31,000 | 3.2 |
| 25 | (22) | 930 | 35,000 | 4.0 |
| 26 | (23) | 900 | 34,000 | 3.6 |
| 27 | (24) | 960 | 39,000 | 4.2 |
| 28 | (25) | 930 | 37,000 | 3.8 |
| 29 | (26) | 900 | 37,000 | 3.7 |
| 30 | (27) | 880 | 34,000 | 3.4 |
| 31 | (28) | 890 | 37,000 | 3.5 |
| 32 | (29) | 910 | 36,000 | 3.2 |
| 33 | (30) | 850 | 33,000 | 3.4 |
| 34 | (31) | 820 | 34,000 | 3.5 |
| 35 | (32) | 850 | 36,000 | 3.7 |
| 36 | (33) | 900 | 39,000 | 3.7 |
| 37 | (34) | 880 | 34,000 | 3.4 |
| 38 | (35) | 850 | 33,000 | 3.5 |
| 39 | (36) | 820 | 37,000 | 3.5 |
| 40 | (37) | 900 | 41,000 | 4.2 |
| 41 | (38) | 880 | 42,000 | 3.6 |
| 42 | (39) | 830 | 39,000 | 3.3 |
| 43 | (40) | 820 | 37,000 | 3.6 |

Light emission brightness and right emission efficiency = values at current voltage of 5 V.

Example 44

Compound (42) was vacuum-deposited on a cleaned glass substrate with an ITO electrode to form a hole-injecting layer having a thickness of 40 nm. Then, Compound (25) as a light-emitting material was vacuum-deposited to form a light-emitting layer having a thickness of 40 nm. Further, 2,5-bis(1-naphthyl)-1,3,4-oxadiazole was vacuum-deposited to form an electron-injecting layer having a thickness of 40 nm. An electrode having a thickness of 150 nm was formed thereon from a magnesium/silver alloy having a magnesium/silver mixing ratio of 10/1, to obtain an organic EL device. Each layer was deposited under vacuum at 10$^{-6}$ Torr at a substrate temperature of room temperature. The organic EL device showed a blue light emission having a brightness of 900 (cd/m$^2$) at a direct current voltage of 5 V, a maximum light emission brightness of 27,300 (cd/m$^2$) and a light emission efficiency of 2.8 (lm/W).

Example 45

An organic EL device was obtained in the same manner as in Example 44 except that Alq3 was used in place for forming an electron-injecting layer. The organic EL device showed a blue light emission having a brightness of 490 (cd/m$^2$) at a direct current voltage of 5 V, a maximum light emission brightness of 15,800 (cd/m$^2$) and a light emission efficiency of 1.9 (lm/W).

Example 46

An organic EL device was obtained in the same manner as in Example 44 except that an aluminum/lithium alloy having an aluminum/lithium mixing ratio of 30/1 was used in place for forming an electrode for cathode. The organic EL device showed a blue light emission having a brightness of 950 (cd/m$^2$) at a direct current voltage of 5 V, a maximum light emission brightness of 29,000 (cd/m$^2$) and a light emission efficiency of 3.0 (lm/W).

Example 47

An organic EL device was obtained in the same manner as in Example 44 except that a hole-injecting layer having a thickness of 5 nm was additionally formed from metal-free phthalocyanine between the ITO electrode and Compound (42). The organic EL device showed a blue light emission having a brightness of 900 (cd/m$^2$) at a direct current voltage of 5 V, a maximum light emission brightness of 22,200 (cd/m$^2$) and a light emission efficiency of 2.5 (lm/W). As compared with the organic EL device obtained in Example 44, the organic EL device obtained in this Example showed a high light emission brightness and was advantageous in driving at a low voltage.

Comparative Example 1

Compound (42) was deposited on a cleaned glass substrate with an ITO electrode to form a hole-injecting layer having a thickness of 50 nm. Then, Alq3 was vacuum-deposited to form a light-emitting layer having a thickness of 50 nm. An electrode having a thickness of 100 nm was formed thereon from a magnesium/silver alloy having a magnesium/silver mixing ratio of 10/1, to obtain an organic EL device. Each layer was deposited under vacuum at 10$^{-6}$ Torr at a substrate temperature of room temperature. The organic EL device showed a light emission having a brightness of 15 (cd/m$^2$) at a direct current voltage of 5 V, a maximum light emission brightness of 12,000 (cd/m$^2$) and a light emission efficiency of 1.1 (lm/W).

Comparative Example 2

Compound (42) was deposited on a cleaned glass substrate with an ITO electrode to form a hole-injecting layer having a thickness of 50 nm. Then, 9,10-diphenylanthracene was vacuum-deposited to form a light-emitting layer having a thickness of 50 nm. An electrode having a thickness of 100 nm was formed thereon from a magnesium/silver alloy having a magnesium/silver mixing ratio of 10/1, to obtain an organic EL device. Each layer was deposited under vacuum at 10$^{-6}$ Torr at a substrate temperature of room temperature. The organic EL device showed a blue light emission having a brightness of 2 (cd/m$^2$) at a direct current voltage of 5 V, a maximum light emission brightness of 2,500 (cd/m$^2$) and a light emission efficiency of 0.15 (lm/W). However, the light emission surface of the device had many dark spots, and the device had an extremely poor product quality as a light-emitting device.

Comparative Example 3

An organic EL device was obtained in the same manner as in Example 4 except that 9,10-diphenylanthracene was used in place as a light-emitting material. The organic EL device showed a blue light emission having a brightness of 60 (cd/M$^2$) at a direct current voltage of 5 V, a maximum light emission brightness of 5,800 (cd/m$^2$) and a light emission efficiency of 0.45 (lm/W). Like Comparative Example 2, however, the light emission surface of the device had many dark spots, and the device had an extremely poor product quality as a light-emitting device.

The organic EL devices obtained in Examples give a maximum light emission brightness of more than 10,000 (cd/m$^2$) and a high light emission efficiency. When the organic EL devices obtained in the above Examples were allowed to continuously emit light at 3 mA/cm$^2$, all the organic EL devices emitted light having a brightness of more than 50% of the initial brightness value for more than 1,000 hours. When the organic EL devices obtained in Comparative Examples were allowed to continuously emit light under the same conditions, the light emission brightness decreased to less than 50% of the initial brightness value within 500 hours. The reason therefor is as follows. The light-emitting materials of the formulae [1] and [2] have a very high fluorescent quantum effect so that the devices for which these materials are adapted can perform light emission with a high brightness in a low voltage range and can have an improved device life. The organic EL device of the present invention achieves improvements in light emission efficiency and brightness, and accomplishes a longer device life, and shall not impose any limitation on light-emitting materials, dopants, hole-transporting materials, electron-transporting materials, sensitizers, resins and electrode materials used in combination with it, nor shall it impose any limitation on the method of producing the device.

The organic EL device for which the light-emitting material of the present invention is adapted shows blue light emission having a higher brightness with a higher light emission efficiency, and has a longer device life, than a conventional organic EL device.

What is claimed is:

1. A light-emitting material for developing an organic EL device, which has the formula [1],

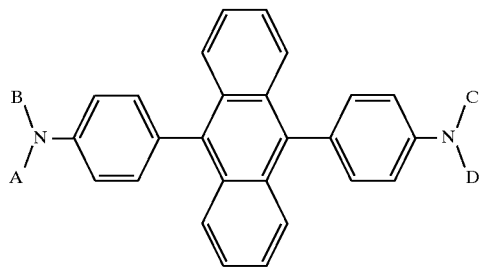

wherein each of A to D is a substituted or nonsubstituted alkyl group, a substituted or nonsubstituted monocyclic group or a substituted or nonsubstituted fused polycyclic group, or a combination of A and B or a combination of C and D is a heterocyclic ring including a nitrogen atom which bonds to an adjacent benzene ring.

2. A light-emitting material according to claim 1, wherein each of A to D in the formula [1] is a substituted or nonsubstituted monocyclic group.

3. A light-emitting material for developing an organic EL device, which has the formula [2],

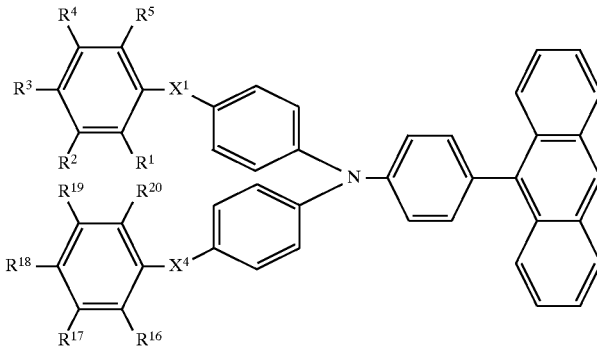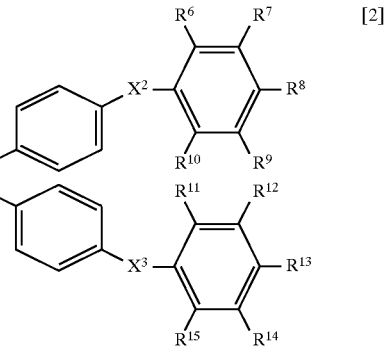

wherein each of $R^1$ to $R^{23}$ is independently a hydrogen atom, a halogen atom, a substituted or nonsubstituted alkyl group, a substituted or nonsubstituted alkoxy group, a substituted or nonsubstituted amino group, a substituted or nonsubstituted monocyclic group, or a substituted or nonsubstituted fused polycyclic group, and each of $X^1$ to $X^4$ is independently a direct bond, O, S, C=O, SO$_2$, (CH$_2$)$_x$—O—(CH$_2$)$_y$, CH$_2$)$_x$—S—(CH$_2$)$_y$, P, P=O, SiR$^{21}$(R$^{22}$), NR$^{23}$, a substituted or nonsubstituted alkylene group or a substituted or nonsubstituted aliphatic ring residue, provided that each of x and y is independently an integer of 0 to 20 while x+y=o in no case.

4. An EL device obtained by forming a light-emitting layer or a plurality of thin organic compound layers including the light-emitting layer between an anode and a cathode, wherein the light-emitting layer contains the light-emitting material recited in claim 1.

5. A device according to claim 4, wherein the device has a layer containing an aromatic tertiary amine derivative and/or a phthalocyanine derivative, formed between the light-emitting layer and the anode.

6. A device according to claim 4, wherein the device has a layer containing a metal complex compound and/or a nitrogen-containing five-membered derivative, formed between the light-emitting layer and the cathode.

7. An EL device obtained by forming a light-emitting layer or a plurality of thin organic compound layers including the light-emitting layer between an anode and a cathode, wherein the light-emitting layer contains the light-emitting material recited in claim 3.

8. A device according to claim 7 wherein the device has a layer containing an aromatic tertiary amine derivative and/or a phthalocyanine derivative, formed between the light-emitting layer and the anode.

9. A device according to claim 5, wherein the device has a layer containing a metal complex compound and/or a nitrogen-containing five-membered derivative, formed between the light-emitting layer and the cathode.

* * * * *